United States Patent [19]

Haeusler

[11] Patent Number: 4,886,908

[45] Date of Patent: Dec. 12, 1989

[54] METHOD OF PREPARING (R)-4-AMINO-3-HYDROXYBUTYRIC ACID

[75] Inventor: Johannes Haeusler, Vienna, Austria

[73] Assignee: Degussa Aktiengesellschaft, Frankfurt, Fed. Rep. of Germany

[21] Appl. No.: 161,941

[22] Filed: Feb. 29, 1988

[30] Foreign Application Priority Data

Mar. 11, 1987 [DE] Fed. Rep. of Germany ....... 3707719

[51] Int. Cl.$^4$ .................. C07C 101/30; C07D 207/12; C07D 207/24; C07D 207/273
[52] U.S. Cl. .................................... 562/567; 548/532; 548/544
[58] Field of Search ............... 548/532, 535, 543, 544, 548/552, 554, 555; 562/524, 526, 553, 567

[56] References Cited

PUBLICATIONS

Chem. Abstracts, vol. 108, No. 21 (1988), 187240s.
The Merck Index, Tenth Edition, 1983, pp. 64, 66, 257–258, Item 432, "γ-Aminobutyric Acid"; item 447, 4-Amino-3-hydroxybutyric Acid; item 1833, Carnitine.
Rajashekhar, B. et al., "Synthesis of Enantiomerically Pure γ-Amino-β-hydroxybutyric Acid Using Malic Acid as the Chiral Precursor", J. Org. Chem. 1985 (50), pp. 5480–5484.
Hausler, J. "A Convenient Synthesis of (R)-γ-Amino-β-hydroxybutyric Acid (GABOB) from Natural (2S,4R)-4-Hydroxyproline", Monatsh. Chem. 1987, 118 (6–7), pp. 865–869 (English Translation).

*Primary Examiner*—Donald B. Moyer
*Assistant Examiner*—Julie K. Parker
*Attorney, Agent, or Firm*—Beveridge, DeGrandi & Weilacher

[57] ABSTRACT

(R)-4-amino-3-hydroxybutyric acid is prepared from the hydrochloride of the methyl ester or ethyl ester of (2S, 4R)-4-hydroxyproline via the intermediary stages of the corresponding, non-isolated (R)-4-hydroxy-1-pyrroline-2-carboxylic acid ester and the isolated (R)-4-hydroxy-2-pyrrolidone. The (R)-4-amino-3-hydroxybutyric acid which is useful for pharmacological purposes is obtainable in a high yield according to this method.

10 Claims, No Drawings

METHOD OF PREPARING (R)-4-AMINO-3-HYDROXYBUTYRIC ACID

THE INVENTION

The present invention relates to a method for preparing (R)-4-amino-3-hydroxybutyric acid in which method the starting material is a (2S,4R)-4-hydroxyproline ester hydrochloride.

BACKGROUND OF THE INVENTION

In a recent publication, J. Org. Chem. 1985, 50, 5480–5484, B. Rajashekhar et al. describe a six step synthesis of γ-amino-β-hydroxybutyric acid using malic acid as the starting material. The authors characterize their method as simpler and more efficient in a 25–30% yield than that of Jung et al. (1980) which involves a nine step synthesis in which ascorbic acid is the starting material and yield is about 10%.

The method of the invention is carried out in a series of steps as set forth herein; namely:

(a) a (2S,4R)-4-hydroxyproline ester hydrochloride of the formula:

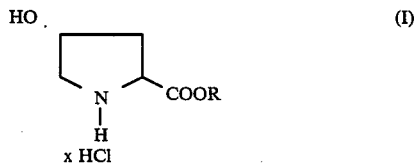

in which R signifies a methyl or ethyl group and the symbol "x" indicates the hydrochloride salt, is converted by being treated in a water-free medium with an alkali metal methoxide or alkali metal ethoxide at first, then t-butyl hypochlorite and finally triethyl amine into the (R)-4-hydroxy-1-pyrroline-2-carboxylic acid ester of the formula:

in which R again has the same meaning already indicated above, (b) the latter compound of formula II is dissolved without further purification in an alkali metal hydroxide solution, the solution is treated with hydrogen peroxide, the resulting reaction mixture is acidified by slowly adding a mineral acid and subsequently desalinated and the thereby formed (R)-4-hydroxy-2-pyrrolidone of the formula:

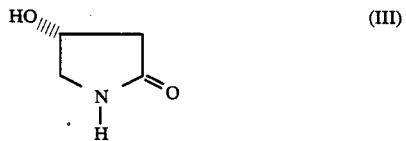

is isolated by concentration using evaporation and thereafter (c) the latter (III) is hydrolyzed with a mineral acid to form (R)-4-amino-3-hydroxybutyric acid of the formula:

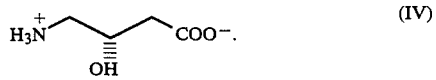

Since the 4-hydroxyproline derivative of formula (I) functioning as the initial starting material can be prepared for its part in a relatively simple manner from the naturally occurring L-4-hydroxyproline, the method of the present invention provides a relatively simple and economical pathway from the latter to (R)-4-amino-3-hydroxybutyric acid.

The (R)-4-amino-3-hydroxybutyric acid itself, obtainable in a high yield in accordance with the method of the present invention, as well as the trimethyl betaine L-carnitine which is readily obtainable therefrom are compounds that have pharmacologically significant applications. It is a known compound having neuromodulator properties for the central nervous system.

In the practical implementation of the method of the present invention, the (2S,4R)-4-hydroxyproline ester must first be released from the (2S,4R)-4-hydroxyproline ester hydrochloride of formula (I) by means of a treatment with an alkali metal methoxide or alkali metal ethoxide. The methoxides and ethoxides of sodium and potassium, which are added advantageously as solution in the corresponding alcohol, are especially well suited for this purpose. The use of a solution of sodium methoxide in absolute methanol is preferred. The alkali metal methoxide or alkali metal ethoxide is preferably used in a 1 to 1.05-fold, especially in a 1 to 1.01-fold molar amount of the (2S,4R)-4-hydroxyproline ester hydrochloride present. The temperature is advantageously between 10° C. and 30° C., preferably between 15° C. and 25° C.

The subsequent treatment of the released (2S,4R)-4-hydroxyproline ester with t-butyl hypochlorite should advantageously be performed in a more non-polar solvent, and therefore, it is advantageous if the alcohol is removed as completely as possible under mild conditions and the residue is taken up in absolute tetrahydrofurane or 1,2-dimethoxyethane or in a mixture of one of these ethers and absolute diethyl ether. The t-butyl hypochlorite is preferably used in a 1 to 1.05-fold, especially in a 1 to 1.02-fold molar amount of the (2S,4R)-4-hydroxyproline ester hydrochloride originally used. The temperature should be maintained advantageously between −40° C. and −20° C.

When the reaction with the t-butyl hypochlorite, which serves for the N-chlorination of the (2S,4R)-4-hydroxyproline ester, has ended, the N-chlorine derivative is subsequently treated without the need for intermediary isolation in the same solvent (mixture) with triethyl amine. The double bond between the nitrogen atom and the carbon atom in the 2-position is formed thereby under dehydrochlorination and the (R)-4-hydroxy-1-pyrroline-2-carboxylic acid ester of formula (II) is created. The triethyl amine is advantageously used in that reaction step in a 1 to 1.05-fold, preferably in a 1 to 1.03-fold molar amount (per mole) of the (2S,4R)-4-hydroxyproline ester hydrochloride originally used. The temperature is advantageously held between −20° C. and +10° C.

It is advantageous if the reaction mixture is allowed to stand for a fairly long time, e.g. overnight (about 16 hours), at a temperature between 0° and +10° C. after the addition of the triethyl amine. Thereafter, the deposited salts are separated and washed with fresh solvent (mixture). The combined filtrates are concentrated by evaporation in a mild manner under reduced pressure.

The (R)-4-hydroxy-1-pyrroline-2-carboxylic acid ester remaining as an oil is subsequently taken up without further purification in an aqueous alkali metal hydroxide solution, preferably sodium hydroxide solution, and reacted with an aqueous solution of hydrogen peroxide. Then, a mineral acid, preferably sulfuric acid or hydrochloric acid, is slowly added. The reaction mixture is allowed to stand for a while at a moderately elevated temperature before the excess hydrogen peroxide is destroyed, e.g. by means of adding an aqueous sodium sulfite solution. In this (b) reaction stage, the alkali metal hydroxide and the hydrogen peroxide are advantageously used in a 1 to 1.05-fold, preferably in a 1 to 1.03-fold molar amount of the (2S,4R)-4-hydroxyproline ester hydrochloride originally used and the mineral acid in an amount which is at least equivalent to the alkali metal hydroxide added. The temperature in this (b) reaction stage is advantageously between 20° C. and 50° C., preferably between 20° C. and 40° C.

The acidified reaction mixture is then desalinated, optionally after some concentration by evaporation under reduced pressure, by being treated with a strongly acidic ion exchanger in the H+ form and with a strongly basic ion exchanger in the HO− form and the desalinated solution is concentrated by evaporation under reduced pressure until dry. The residue is advantageously treated several times with absolute ethanol and again concentrated by evaporation in order to remove residual water and is finally treated with absolute diethyl ether. The resulting crystals of (R)-4-hydroxy-2-pyrrolidone of formula (III) obtained can be sublimated for further purification in a high vacuum.

Finally, the (R)-4-hydroxy-2-pyrrolidone of formula (III) is hydrolyzed in excess mineral acid, preferably sulfuric acid and especially hydrochloric acid. The mineral acid is advantageously added in a 5 to 10-fold, preferably a 5 to 6-fold molar amount (per mole) of the (R)-4-hydroxy-2-pyrrolidone present and in a concentration between 4N and 6N. The hydrolysis temperature can be e.g. between 90° C. and the reflux temperature of the reaction mixture. The hydrolysis is preferably performed by heating under reflux.

After the hydrolysis has been completed, the reaction mixture, for example, can be worked up in such a manner that it is treated with a strongly acidic ion exchanger in the H+ form and the (R)-4-amino-3-hydroxybutyric acid is eluted with diluted, aqueous ammonia solution. The eluate is then concentrated by evaporation under reduced pressure until dry. The remaining (R)-4-amino-3-hydroxybutyric acid of formula (IV) can be recrystallized for further purification, optionally with the addition of activated carbon, from a water/ethanol mixture.

DETAILED DESCRIPTION OF INVENTION

The invention is explained in more detail by the following example. The melting points were determined on a hot-stage microscope according to the method of Kofler and the specific rotations were measured with a polarimeter 241 of the Perkin-Elmer company.

EXAMPLE

Reaction stage (a):

7.24 g (40 mmoles) rigorously dried (2S,4R)-4-hydroxyproline methyl ester hydrochloride were reacted in a flask with 40.0 ml of a 1N solution of sodium methoxide in water-free methanol while being swirled for agitation. The resulting suspension was concentrated by evaporation in a rotary evaporator at a bath temperature of 25° C. until an oily consistency of the residue was achieved. This residue was taken up and mixed in 120 ml of a mixture of absolute tetrahydrofurane and absolute diethyl ether (proportion by volume 2:1) and reacted at a temperature of −40° C. under agitation with 4.0 g (40.5 mmoles) freshly distilled t-butyl hypochlorite. The solution was allowed to reach −20° C. within 45 minutes and then 5.7 ml (41 mmoles) water-free triethyl amine were added. The reaction mixture was left at −20° C. for 1 hour longer and then stored overnight at approximately +5° C. in a refrigerator. The crystallized triethyl amine hydrochloride and sodium chloride were removed by suction and washed with fresh solvent mixture. The combined filtrates were concentrated by evaporation in a mild manner under reduced pressure. A specimen of the (R)-4-hydroxy-1-pyrroline-2-carboxylic acid methyl ester remaining in oily form was examined by thin-layer chromatography on a DC plate with silica gel 60 of the Merck company using a mixture of chloroform and methanol (proportion by volume 9:1) as mobile solvent. The $R_f$ value was 0.36.

Reaction stage (b):

The oil remaining in reaction stage (a) was rapidly reacted without further purification with 41 ml 1N sodium hydroxide solution and 4.1 ml (40 mmoles) of a 30% by weight aqueous hydrogen peroxide solution. Within 20 minutes, 4.5 ml 10N sulfuric acid was added dropwise and the reaction mixture was maintained for 45 minutes at a temperature of 40° C. Then, the excess hydrogen peroxide was destroyed by means of the addition of a little sodium sulfite and the solution was somewhat concentrated by evaporation under reduced pressure. Then the solution was desalinated by being treated with a strongly acidic ion exchanger in the H+ form (Dowex 50 W×8) and with a strongly basic ion exchanger in the HO− form (Dowex I), each time in a column of 180 mm×30 mm. The now neutral solution was concentrated by evaporation under reduced pressure until dry. The residue was taken up several times in absolute ethanol and concentrated by evaporation again in order to remove residual water and finally treated with absolute diethyl ether. The 3.67 g (R)-4-hydroxy-2-pyrrolidone obtained at first were sublimated in a high vacuum in a bulb tube at an air bath temperature of 150° C. to 160° C. There were obtained 3.60 g (89% of theory in relation to (2S,4R)-4-hydroxyproline methyl ester hydrochloride used) colorless crystals with a melting point of 156°–158° C. and an $[\alpha]_D^{20}$ of +59.5° (c=1.14, H$_2$O).

Reaction stage (c):

A solution of 3.60 g (35.6 mmoles) (R)-4-hydroxy-2-pyrrolidone in 60 ml 4N hydrochloric acid was heated 4 hours under reflux and then concentrated almost completely by evaporation under reduced pressure. Thereafter, the residue was free of excess hydrochloric acid by being repeatedly dissolved in water and reconcentrated by evaporation. The residue was then dissolved in water again and passed over a 180 mm×30 mm column filled with a strongly acidic ion exchanger in the H+ form (Dowex 50 W×8). The ion exchanger was eluted with a 1N aqueous ammonia solution, the eluate was concentrated by evaporation under reduced pressure until dry and the residue was recrystallized under the addition of activated carbon from a water/ethanol mixture. There was obtained 3.98 g (94% of theory) colorless (R)-4-amino-3-hydroxybutyric acid with a melting point of 213°–215° C. (decomposition) and an $[\alpha]_D^{20}$ of $-20.5°$ (c=2.08, H$_2$O).

Thus, the total yield in relation to the originally used (2S,4R)-4-hydroxyproline methyl ester hydrochloride was approximately 84% of theory.

Typically, hydrogen peroxide is used in 3–30% by weight aqueous solutions and the mineral acids are used in 2.0–10.0N. Lye is generally preferred as the alkali metal hydroxide.

Further variations and modifications of the foregoing will become apparent to those skilled in the art from a reading hereof and are intended to be encompassed by the appended claims.

German priority application P 37 07 719.8 is relied on and incorporated herein.

I claim:
1. A method for preparing (R)-4-amino-3-hydroxybutyric acid, comprising:
   (a) reacting the compound (2S,4R)-4-hydroxyproline ester hydrochloride of the formula:

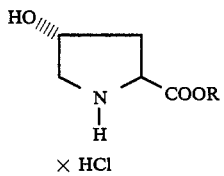

in which formula R is a methyl or ethyl group,
in a water-free medium with an alkali metal methoxide or alkali metal ethoxide as solution in the corresponding alcohol as an initial step, then treating with t-butyl hypochlorite for N-chlorination and finally treating with triethyl amine for dehydrochlorination to thereby obtain a compound (R)-4-hydroxy-1-pyrroline-2-carboxylic acid ester of the formula:

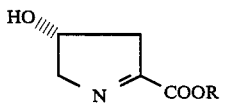

in which R again has the same meaning as above,
   (b) thereafter dissolving said compound of formula II without further purification in an alkali metal hydroxide solution, adding to said solution hydrogen peroxide to obtain a reaction mixture, acidifying said reaction mixture by slowly adding a mineral acid, subsequently desalinating and isolating the resulting (R)-4-hydroxy-2-pyrrolidone of the formula:

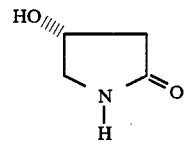

by evaporation concentration and thereafter
   (c) hydrolyzing said pyrrolidone III with a mineral acid to (R)-4-amino-3-hydroxybutyric acid of the formula:

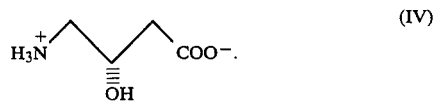

2. The method according to claim 1, wherein in reaction stage (a) the treatment with t-butyl hypochlorite and triethyl amine is performed in absolute tetrahydrofurane or 1,2-dimethoxyethane or in a mixture of one of these ethers and absolute diethyl ether.

3. The method according to claim 1, wherein in reaction stage (a) the alkali metal methoxide or alkali metal ethoxide, the t-butyl hypochlorite and the triethyl amine are each added in a 1 to 1.05-fold molar amount of the (2S,4R)-4-hydroxyproline ester hydrochloride used.

4. The method according to claim 1, wherein in reaction stage (a) the treatment with the alkali metal methoxide or alkali metal ethoxide is performed at a temperature between 10° C. and 30° C.

5. The method according to claim 1, wherein in reaction stage (a) the treatment with the t-butyl hypochlorite is performed at a temperature between −40° and −20° C.

6. The method according to claim 1, wherein in reaction stage (a) the treatment with the triethyl amine is performed at a temperature between −20° C. and +10° C.

7. The method according to claim 1, wherein in reaction stage (b) the alkali metal hydroxide and the hydrogen peroxide are each added in a 1 to 1.05-fold molar amount of the (2S,4R)-4-hydroxyproline ester hydrochloride originally used and the mineral acid is added in an amount which is at least equivalent to the alkali metal hydroxide.

8. The method according to claim 1, wherein reaction stage (b) is performed at a temperature between 20° C. and 50° C.

9. The method according to claim 1, wherein in reaction stage (c) the mineral acid is added in a 5 to 10-fold molar amount of the (R)-4-hydroxy-2-pyrrolidone present.

10. The method according to claim 1, wherein reaction stage (c) is performed at a temperature between 90° C. and the reflux temperature of the reaction mixture.

* * * * *